(12) United States Patent
Iannone

(10) Patent No.: US 9,791,364 B2
(45) Date of Patent: Oct. 17, 2017

(54) SYSTEMS AND METHODS FOR MEASURING ABSORBED HUMIDITY IN A COMPOSITE MATERIAL

(71) Applicant: ALENIA AERMACCHI S.p.A., Rome (IT)

(72) Inventor: Michele Iannone, Torre Annunziata (IT)

(73) Assignee: ALENIA AERMACCHI S.P.A., Rome (IT)

( * ) Notice: Subject to any disclaimer, the term of this patent is extended or adjusted under 35 U.S.C. 154(b) by 81 days.

(21) Appl. No.: 14/433,057

(22) PCT Filed: Oct. 9, 2013

(86) PCT No.: PCT/IB2013/059227
§ 371 (c)(1),
(2) Date: Apr. 2, 2015

(87) PCT Pub. No.: WO2014/057429
PCT Pub. Date: Apr. 17, 2014

(65) Prior Publication Data
US 2015/0260637 A1 Sep. 17, 2015

(30) Foreign Application Priority Data
Oct. 9, 2012 (IT) .............................. TO2012A0878

(51) Int. Cl.
*G01N 19/10* (2006.01)
*G01N 33/44* (2006.01)
*G01N 33/00* (2006.01)

(52) U.S. Cl.
CPC ........... *G01N 19/10* (2013.01); *G01N 33/442* (2013.01); *G01N 2033/0003* (2013.01)

(58) Field of Classification Search
CPC .... G01N 33/246; G01N 25/56; G01N 27/223; G01N 2291/02845; G01N 29/036; G01N 2291/0256; G01N 27/185; G01N 30/66; G01N 27/18; G01N 25/60; G01N 25/68; G01N 19/10; G01N 33/442;
(Continued)

(56) References Cited

U.S. PATENT DOCUMENTS 5,443,884 A * 8/1995 Lusignea ........... B29D 99/0089
156/197
6,313,646 B1 * 11/2001 Davis ..................... G01N 17/02
204/404
(Continued)

OTHER PUBLICATIONS

Mark E. Tuttle, Moisture Ingression in honeycomb sandwich composites due to exposure to humidity, Dec. 2010, University of Washington—Department of Mechanical Engineering, pp. 1-14.*
(Continued)

*Primary Examiner* — John Fitzgerald
*Assistant Examiner* — Truong D Phan
(74) *Attorney, Agent, or Firm* — Robert E. Alderson, Jr.

(57) ABSTRACT

Systems are provided for measuring absorbed humidity in a composite material, including an item of composite material which includes a plurality of plies of material consolidated through the action of pressure and heat, wherein each ply of material is formed from a resin matrix reinforced with a fiber material, an insert embedded in the composite material, which is positioned in an interface zone between a first and a second ply of material, and in which at least one cavity is formed, in fluid communication with first and second ply of material, and an ambient humidity sensor positioned inside the cavity, capable of providing a signal indicating the humidity content in the atmosphere present inside the cavity. Corresponding methods are also provided.

4 Claims, 1 Drawing Sheet

(58) Field of Classification Search
CPC .... G01N 9/36; G01N 21/3554; G01N 27/048; G01N 27/121; G01N 2201/0238; G01N 31/222; G01N 25/62; G01N 27/225; G01N 2033/0003; B60H 1/00785; B60S 1/0822; B60S 1/0818; B60S 1/0833; B32B 17/10036
USPC .... 73/24.04, 25.04, 29.01, 73, 29.02, 29.05; 219/494, 544; 340/602; 318/643
See application file for complete search history.

(56) References Cited

U.S. PATENT DOCUMENTS

| | | | | |
|---|---|---|---|---|
| 2005/0146076 | A1* | 7/2005 | Alexander | D03D 1/0088 264/257 |
| 2008/0128553 | A1* | 6/2008 | Brown | B64C 1/26 244/124 |
| 2010/0096383 | A1* | 4/2010 | Apicella | B32B 3/08 219/494 |
| 2010/0151189 | A1* | 6/2010 | Chakrabarti | E04C 2/296 428/119 |
| 2011/0247958 | A1* | 10/2011 | Lucas | B29C 70/521 206/524.6 |
| 2012/0121848 | A1* | 5/2012 | Gold | B32B 1/04 428/76 |

OTHER PUBLICATIONS

G. Mensitieri, CR-INSTM,—University of Naples Federico II, M. Iannone, Alenia Aeronautica s.p. a., Modelling Accelerated Ageing in Polymer Composites, Ageing of Composites, 2008, pp. 224-280, Woodhead Publishing Limited, CRC.

Jean Rouchon, Certification of Large Airplane Composite Structures, Recent Progress and New Trends in Compliance Philosophy, 17th ICAS congress, 1990, pp. 1-9, France.

Michele Iannone, Composite Materials for Aeronautic Application, Wiley Encyclopedia of Composites, Second Edition, 2012, pp. 1-14, Edited by Luigi Nicolais and Assunta Borzacchiello, John Wiley & Sons. Inc.

D. Larobina, G. Mensitieri, A. Aldi, E. Calvi, M, Iannone, F. Manzi, L. Nicolais, An integrated Approach to Analyze Long-term Moisture Transport in Honeycomb-core Sandwich Panels, Journal of Composite Materials, 2010, pp. 2473-2486, vol. 44, No. 21, the Author(s), www.sagepub.co.uk/journalsPerrnissions.nav, DOI: 10.1177/0021998310373522, Italy.

Mark E. Tuttle, Moisture Ingression in Honeycomb Sandwich Composites due to exposure to Humidity, International SAMPE Symposium and Exhibition (Proceedings), 2010, pp. 1-14, SAMPE 2010 Conference and Exhibition New Materials and Processes for a New Economy, Seattle, WA., XP008163747.

S. H. Myhre, J.D. Labor, S.C. Aker, Moisture Problems in Advanced Composite Structural Repair, Composites, Jul. 1962, pp. 289-297, 0010-4361/82/030289-09, Butterworth & Co (Publishers) Ltd.

Thomas Carlsson, Petri Konttinen, Janne Halme, Peter Lund, Method for Characterization of Moisture Ingress at Laminated Glass/Polymer Encapsulant interfaces, 21st European Photovoltaic Solar Energy Conference, Sep. 4-8, 2006, pp. 2061-2064.

\* cited by examiner

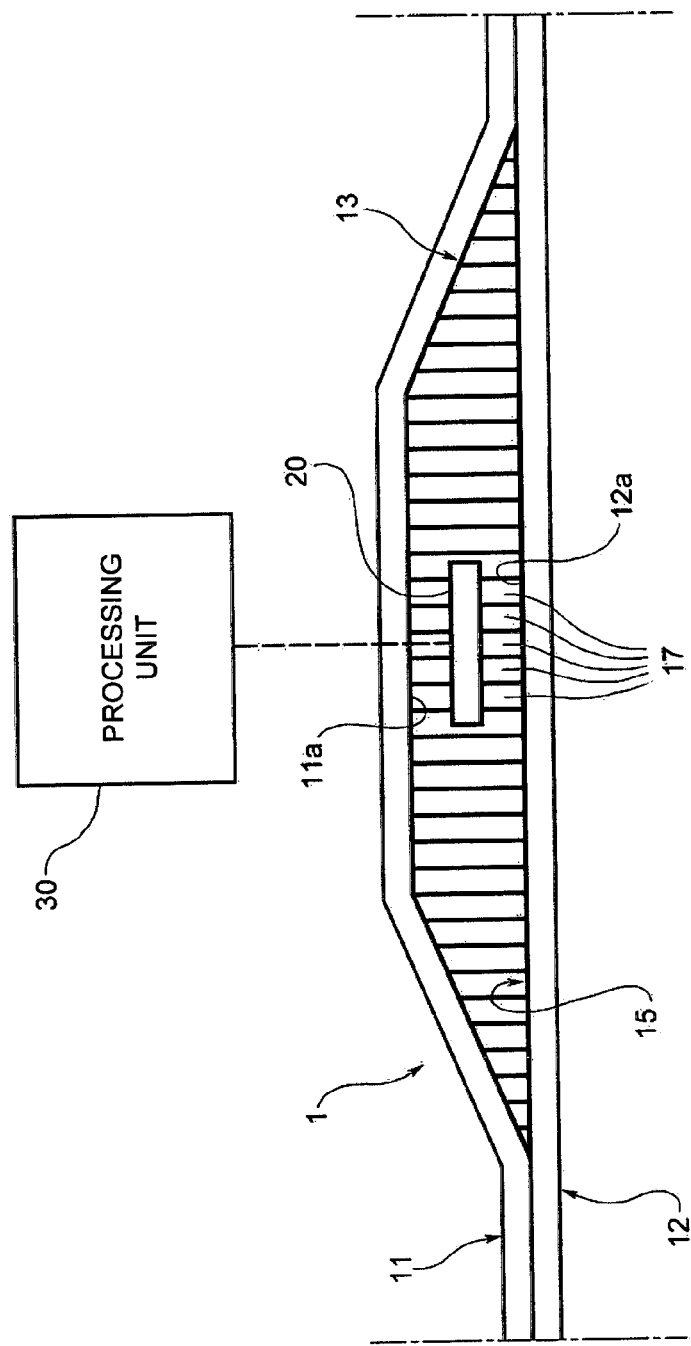

SYSTEMS AND METHODS FOR MEASURING ABSORBED HUMIDITY IN A COMPOSITE MATERIAL

CROSS-REFERENCE TO RELATED APPLICATIONS

This application is a National Phase Application of PCT International Application No. PCT/IB2013/059227, International Filing Date, Oct. 9, 2013, claiming priority to Italian Patent Application No. TO2012A000878, filed Oct. 9, 2012, each of which is hereby incorporated by reference in its entirety.

FIELD OF THE INVENTION

The present invention relates in general to techniques for measuring absorbed humidity in composite materials having a polymeric matrix.

BACKGROUND OF THE INVENTION

As is well known, polymeric materials have a macromolecular structure, that is it is characterized by long polymeric chains with variable relative mobility depending on the structure itself, but in all cases such as to allow the access of molecules of substances of lower molecular weight, which insert themselves between the macromolecules forming a real solution.

Obviously the quantity of such substances depends on the molecular nature of the polymer and of the material of low molecular weight. Also, the interaction can be of a chemical and/or physical type.

Chemical interaction, for some chemically more reactive substances, such as acids and/or some organic solvents, can lead to a modification of the polymer itself and in some cases to real dissolution. Conversely, physical interaction is linked to mixing of an essentially reversible type; a solution is created between polymer and low molecular weight substance, with modified physical properties compared to the pure polymer. Since these are substances of low molecular weight, they generally have the effect of facilitating relative movements between the macromolecules, generally producing a lowering of the glass transition temperature ($T_g$); from a mechanical point of view, the values of the plastic flow $\sigma_y$ (tensile) and $\tau_y$ (shear) stress generally decrease, and the elastic modulus E (tensile elastic, or Young's, modulus), and the shear elastic modulus (G), generally decrease. The totality of all these effects is generally termed "plasticization".

The plasticization depends on the nature of the polymer and on the dissolved low molecular weight substance, and on the quantity of that substance.

The plasticizing substances include organic solvents (for example: MEK, methanol, ethanol, hexane and acetone), and also water. If the polymer is immersed in the plasticizing liquid, it tends to absorb it, and absorbs a certain quantity of it in a time which depends on the rate of diffusion of that substance in the polymer. When an equilibrium situation is reached, that is such as not to have further entry of the plasticizer into the polymer (in reality, at the molecular level, the number of molecules entering is equal to that of those emerging), it is said that the "saturation" content of the plasticizer has been reached, which depends on the chemical nature of the polymer and of the plasticizer and can depend on the temperature.

When the polymer is immersed in a medium having a partial content of plasticizer, the saturation quantity is a function of the percentage of plasticizer present in the medium; more precisely in thermodynamic terms the activity of the plasticizer is referred to. In the case of gaseous mixtures, the activity is linked to the partial pressure; if x is the volumetric fraction of the plasticizer, the partial pressure is equal to $x \cdot \pi$, where $\pi$ is the pressure of the mixture. In the case of water dispersed in air in gaseous form, when there is equilibrium between the gaseous water and the liquid water the activity of the gaseous water is equal to that of the liquid water. In this case, it is stated that the medium is saturated with water and the relative humidity is equal to 100%, and the partial pressure of the water in the gaseous phase is equal to the vapour pressure of the liquid water at the same temperature.

For polymers exposed to media wherein water is present, there is, to a good approximation, a linear relationship between the relative humidity and the percentage quantity of water absorbed by the polymer at saturation.

However, as regards the variability of water absorbed as a function of the temperature, in general the dependence in relation to the temperature is not very great; for the epoxy resins used as matrices for structural composites in the aeronautic industry, the percentage of water absorbed at saturation by the resin immersed in water (or equivalently in humid air at 100% humidity) varies depending on the type of resin. Expressed as $\Delta$weight/weight, it typically varies from 1 to 3%, and is almost constant, for the same resin, in the temperature range from 25° to 80° C. [1, 2].

However, the rate at which saturation is reached in the different environments is controlled by the diffusion of the water within the polymer, and is thus a function of the diffusion coefficient, which depends exponentially on the temperature. Integration of the diffusion law leads to the identification of a dependence of the saturation time on the thickness of the quadratic type.

All of the aforesaid leads to the consideration that polymeric materials, such as for example the matrix of composites with a polymeric matrix, are liable in time to absorb atmospheric water to an extent depending on the atmospheric conditions prevailing. In view of the variability of the conditions, it is necessary as a precaution to consider the most unfavourable conditions, which for aeronautic applications have been agreed to be 28° C. and 85% relative humidity for the entire lifetime of the aircraft (typically 30 years). For the majority of composite structures, this involves the hypothesis of assuming a saturation on the scale of at least 85% for certification purposes [3].

As regards the temperatures, generally the minimum temperature (at altitude) is −55° C., and the maximum (on the ground, intense solar exposure) is 80° C.

From what has been said concerning plasticization, the effect of high temperature operates in the same direction as the absorption of moisture; hence the certification of materials and of structures is carried out by assessing the material at high temperature and after absorption of moisture (condition "hot wet"), and at low temperature generally without absorption of moisture (condition "cold dry").

The need to add these conditions to the aeronautical certification plans, already very onerous because of the mechanical tests at ambient temperature (which in any case concern test pieces, parts, elements, subcomponents and complete components), is very costly in terms of additional experimental activity (even for the exposure of the test samples) and time. Indeed, from the aforesaid, the absorption is very slow, and simulating absorption over thirty years at ambient temperature requires several months even with recourse to accelerated aging (at high temperature).

From the aforesaid, the quantity of moisture which is typically contained in aeronautical composite structures is very variable, and it is even quite rare that it reaches values in equilibrium with an environment with a high percentage humidity. This is because typically the humidity is not so high, and because under the conditions when the aircraft is parked in the sun heating of the irradiated parts occurs which brings them to a temperature greater than ambient, with the accelerated desorption effect due to the heating. Hence, if a direct measurement of the moisture contained in the composite were possible, typically expressed as Δweight/weight, it would be possible to imagine certification of the structures under non-wet conditions (for example at 50% saturation, the condition known as "ambient"), subject to periodical checking on the aircraft composite structure monitored that that percentage is not exceeded. However, at the current state of knowledge, there is no known method for direct measurement of the quantity of humidity. In reality, a very simple method, commonly used in the laboratory, is that of weighing the parts which have absorbed moisture and then to weigh them again after a desorption in a dry environment at high temperature (for example an oven at circa 80° C.), but this method, which gives an average value over the entire thickness of the composite, is obviously not applicable to aeronautical parts in service. Methods based on the measurement of the conductivity or the dielectric properties, or even based on infrared spectrometry, have also been tried, but the results obtained are not satisfactory, above all because the presence of the carbon fibres renders all the properties associated with the resin much more difficult to read; for example, in a composite the thermal or electrical conductivity depends mainly on the fibres, and slight variations in the conductivity of the resin have a very limited effect on the conductivity of the composite. As regards spectrometry, it is difficult to obtain quantitative evaluations of the presence of water from a spectrum obtained on polymerized resin, in particular in the presence of reinforcing fibres.

However, the humidity can be measured with good precision in air, with standardized methods such as that linked to the deformation of a hygrometric substance (for example a hair), or to the comparative reading of the wet bulb and dry bulb temperature or (more recently) with a capacitive humidity sensor, that is a condenser which changes its capacity as a function of the humidity of the air between the opposed conductors (or plates).

SUMMARY OF THE INVENTION

One purpose of the present invention is that of providing a system for the measurement of the internal humidity of composite material, which may provide the possibility of in-service measurement of the absorbed humidity. Such a system would allow the certification of the structures under conditions more advantageous than wet conditions, with the sole condition of a periodical check of the humidity in service and, in (improbable) case of the humidity level established by the certification being exceeded, of a dehumidification intervention in a hot environment or with local heating.

This would in turn involve advantages of savings in the weight of the structure, in that admissible values would be used (that is the properties of the material used for the design process) under conditions more advantageous and hence higher than the wet conditions. More precisely, to a percentage increase x % in the dimensioning property there corresponds a weight decrease of the same extent. The decrease in weight also involves an equivalent saving in the cost of the material used (including the recurrent production cost, proportional to the quantity of material used). Finally, the possibility of certification under "dry" conditions also involves a simplification and a consequent saving on the process of certification of the composite structures, with a significant reduction in the non-recurrent costs for creation of a new aircraft, in particular through the possibility of certificating the structures without performing tests under wet conditions nor at the level of test pieces, nor of sub-components and components.

According to the present invention, the aforesaid purpose is achieved by means of a system for measuring absorbed humidity in a composite material, including
    an item of composite material comprising a plurality of plies of material consolidated through the action of pressure and heat, wherein each ply of material is formed from a resin matrix reinforced with a fibre material,
    an insert embedded in said composite material, which is positioned between a first and a second of said plies of material, in a limited interface zone outside which said first and second plies of material are mutually contiguous, at least one cavity being formed in said insert in fluid communication with said first and second plies of material, and
    an ambient humidity sensor positioned inside said cavity, and capable of providing a signal indicating the humidity content in the atmosphere present inside said cavity.

Also subject matter of the invention is a method for measuring absorbed humidity in a composite material, including the following steps:
    providing an item of composite material comprising a plurality of plies of material consolidated through the action of pressure and heat, wherein each ply of material is formed from a resin matrix reinforced with a fibre material, and an insert embedded in said composite material, which is positioned between a first and a second of said plies of material, in a limited interface zone outside which said first and second plies of material are mutually contiguous, at least one cavity being formed in said insert, in fluid communication with said first and second plies of material, an ambient humidity sensor being positioned inside said cavity,
    by means of said ambient humidity sensor, providing a signal indicating the humidity content in the atmosphere present inside said cavity, and
    determining the content of absorbed humidity in the composite material at the level of said interface zone as a function of the humidity content present inside said cavity.

Particular embodiments form the subject matter of the dependent claims, the content whereof is to be understood as an integral part of the present description.

The concept on which the invention is based is that of creating within the parts in composite material whose humidity content it is desired to measure a space free from the composite which is however in contact with the composite itself. This free space is progressively filled with air owing to porosity and diffusion, and contains a quantity of humidity in equilibrium, or which rapidly comes into equilibrium, with the surfaces of the plies of material in contact with the aforesaid space. Hence, with a measurement of humidity in the gas phase performed with a humidity measurement device it is possible to determine, by standard calculations, the humidity absorbed in the adjacent plies of composite material.

Further characteristics and advantages of the invention will be disclosed in more detail in the following detailed description of one embodiment thereof, given by way of non-limiting example, with reference to the appended drawing which shows diagrammatically one example of a system for measuring absorbed humidity in a composite material according to the invention.

BRIEF DESCRIPTION OF THE DRAWING

FIG. 1 is a schematic representation of composite material, such as a panel, which constitutes a component located on board an aircraft, such as a fuselage panel.

FIG. 1 shows an item 1 of composite material, such as for example a panel, which may for example constitute a component located on board an aircraft, such as for example a fuselage panel. The item 1 comprises, in a manner known per se, a plurality of plies of material 11, 12 consolidated through the action of pressure and heat (two plies only being for simplicity shown in the FIGURE), wherein each ply of material is formed from a resin matrix reinforced with a fibre material. The polymeric matrix can be thermoplastic or thermosetting and is reinforced with fibres, in particular long fibres, for example of carbon, glass or Kevlar.

DETAILED DESCRIPTION

There is provided an insert 13 embedded in the composite material, which is positioned in an interface zone 15 between two of the aforesaid plies of material. The extent of the interface zone 15 in which the insert 13 is positioned is limited, in the sense that it is small compared to the surface extent of the plies of material 11, 12. Correspondingly to the interface zone 15 occupied by the insert 13, the plies of material 11, 12 are spaced apart because of the thickness of the insert 13, while outside the interface zone 15 the plies of material 11, 12 are mutually contiguous. Inside the insert 13 at least one cavity 17 is formed, in fluid communication with the plies of material 11, 12 between which the insert 13 is interposed.

Preferably, the insert 13 has a honeycomb structure, for example of metallic or polymeric (aramid) material, in which the aforesaid cavity 17 is formed from one or more cells of the honeycomb structure.

An important characteristic of the honeycomb structure consists in the fact that this allows the creation of an internal volume not separate from the composite, something which would not be possible if for example a closed box element were used; moreover, if the honeycomb is dimensioned correctly, it prevents the crushing of the internal volume during the phase of polymerization of the plies of material. The insert 13 can be of small dimensions; for example, it can have a thickness of ¼" (about 6 mm), and planar dimensions 50×50 mm. This is moreover advantageously tapered along its peripheral border. The invention is however not limited to one specific structure and shape of the insert 13, provided that the latter is capable of maintaining a cavity in contact with the composite material.

An ambient humidity sensor 20 is positioned inside the cavity 17. This sensor is capable of providing a signal indicating the humidity content in the atmosphere present inside the cavity 17.

A processing unit 30 is operatively connected to the ambient humidity sensor 20, for example by an electric wire, optical fibre or wireless connection. The processing unit 30 reads the signal deriving from the sensor 20 and determines the content of absorbed humidity in the composite material as a function of the humidity content present inside the cavity 17.

As disclosed above, the concept on which the invention is based is that of creating within the parts in a composite the humidity whereof it is desired to measure a space free from the composite, which is however in contact with the composite itself. The use of the insert allows the creation of an "empty" zone, which in reality is progressively filled with air owing to porosity and diffusion, and which contains a quantity of humidity in equilibrium, or which rapidly reaches equilibrium, with the surfaces 11a, 12a of the adjacent plies 11 and 12. It may be seen that the surfaces in question, owing to how the sandwich zone is created, are the continuation of the totality of the interface surfaces of the plies 11 and 12 of the laminated solid. The quantity of water in weight terms contained in the gaseous phase in the sandwich zone is very low, compared to that contained in the laminated solid. To give a numerical example, considering a composite at 25° C. which has a saturation percentage content $\Delta$weight/weight=2%, and considering a thickness of an inserted empty zone of 6 mm, wherein the air is saturated (since in equilibrium with a surface which is itself saturated), the partial pressure of the water is equal to the vapour pressure at 25° C., namely 0.0313 atm. By simple calculations based on Avogadro's law, it may be concluded that the quantity of water contained in a thickness of 6 mm is equivalent to that contained in 0.004 mm of composite, and hence the equivalent variation in thickness due to the addition of the void in the insert is practically negligible. As regards the quantity of water contained in the honeycomb, which typically has a density of circa 0.05 g/cc, in 6 mm of thickness of honeycomb it is roughly equivalent to that contained in 0.2 mm of composite, hence roughly equivalent to one additional ply of composite. Account should also be taken of the fact that the thickening due to the presence of the insert does not affect the whole structure, but only a very limited area thereof (provided that it is sufficient to contain the sensor). With all these considerations, it can be concluded that the percentage humidity contained on the surfaces 11a and 12a is practically equal to that contained in the remaining part of the totality of the interface surfaces of the plies 11, 12 of the laminate [4].

Hence a measurement of humidity in the gaseous phase performed with the ambient humidity sensor 20 is directly correlatable with the humidity absorbed at the level of the interface between the plies 11 and 12 of the panel (below: "interface 11-12") corresponding to which the sensor 20 is positioned; more precisely, the humidity absorbed by the panel in the solid phase at the level of the interface 11-12 is equal to that absorbed by the composite at saturation in an environment at 100% relative humidity, expressed as $\Delta$weight/weight*percentage humidity multiplied by the relative humidity measured in the zone of the insert. To give a numerical example, if the value $\Delta$weight/weight of water of a composite in an environment saturated with water at equilibrium is 2%, if the sensor 20 measures 50% relative humidity, it means that the absorption of water in the composite at the level of the interface 11-12 $\Delta$weight/weight is 2%*50/100=1%.

Advantageously, the use of cavities with sensors positioned at different points of the thickness of the composite material to ascertain a humidity profile inside the composite material is also possible. For situations where at equal depth it is possible that the humidity absorbed varies as a function of the position on the surface, it is conceivable to position cavities with sensors also in different topological positions of the interface surfaces of the composite material.

Naturally, with the principle of the invention remaining unchanged, the embodiments and the details of implementation could be varied considerably compared to what has been described and illustrated purely by way of non-limiting example, without thereby departing from the protected scope of the invention as described and claimed herein.

LITERATURE REFERENCES

1. G. Mensitieri/M. Iannone, "Modeling accelerate ageing in polymer composites", Chapter 9 of: "Ageing of Composites" Woodhead Publishing Limited, September 2008
2. M. Iannone—Composite Materials for Aeronautical Applications in Encyclopedia of Composites, John Wiley and Sons, second edition (2012)
3. J. Rouchon, "Certification of large airplane composite structures, recent progress and new trends in compliance philosophy", 17th ICAS Congress, Stockholm, 1990
4. D. Larobina, G. Mensitieri, A. Aldi, E. Calvi, M. Iannone, F. Manzi and L. Nicolais, "An Integrated Approach to Analyze Long-term Moisture Transport in Honeycomb-core Sandwich Panels", Journal of Composite Materials, Vol. 44, No. 21/2010 2473-2486

The invention claimed is:

1. A system for measuring absorbed humidity in a composite material, comprising:
   a composite material which comprises a plurality of plies of material consolidated through the action of pressure and heat, wherein each ply of material is formed from a resin matrix reinforced with a fibre material, each ply of material having a surface extent and a thickness,
   an insert embedded in said composite material, which is positioned in an interface zone between a first and a second of said plies of material, said interface zone being limited to an area smaller than the surface extent of the first and second plies of material, wherein in the interface zone, said first and second plies of material are spaced apart from each other by the insert, and outside of the interface zone, said first and second plies of material are mutually contiguous with each other, at least one cavity being formed in said insert, in fluid communication with said first and second plies of material,
   an ambient humidity sensor positioned inside said cavity capable of providing a signal indicating humidity content in an atmosphere present inside said cavity, and
   a processing unit operatively connected to said ambient humidity sensor, said processing unit being configured to measure the humidity content in the atmosphere present inside said cavity, based on said signal, and determine content of absorbed humidity in the composite material at level of interface surfaces of said first and second plies of material where said first and second plies of material are mutually contiguous with each other, based on the measured humidity content in the atmosphere present inside said cavity.

2. The system of claim 1, wherein said insert has a honeycomb structure, said cavity being constituted by one or more cells of the honeycomb structure.

3. A method for measuring absorbed humidity in a composite material, comprising the steps of:
   providing an item of composite material which comprises a plurality of plies of material consolidated through the action of pressure and heat, wherein each ply of material is formed from a resin matrix reinforced with a fibre material, each ply of material having a surface extent and a thickness, and an insert embedded in said composite material, which is positioned in an interface zone between a first and a second of said plies of material, said interface zone being limited to an area smaller than the surface extent of the first and second plies of material, wherein in the interface zone, said first and second plies of material are spaced apart from each other by the insert, and outside of the interface zone, said first and second plies of material are mutually contiguous with each other, at least one cavity being formed in said insert, in fluid communication with said first and second plies of material, within which an ambient humidity sensor is positioned,
   said ambient humidity sensor providing a signal indicating humidity content in an atmosphere present inside said cavity,
   measuring the humidity content in the atmosphere present inside said cavity, based on said signal, and determining content of absorbed humidity in the composite material at a level of interface surfaces of said first and second plies of material where said first and second plies of material are mutually contiguous with each other, based on the measured humidity content in the atmosphere present inside said cavity.

4. The method of claim 3, wherein said insert has a honeycomb structure, said cavity being constituted by one or more cells of the honeycomb structure.

* * * * *